United States Patent [19]
Arendt

[11] Patent Number: 4,857,505
[45] Date of Patent: Aug. 15, 1989

[54] SUSTAINED RELEASE COMPOSITIONS FOR PARENTERAL ADMINISTRATION AND THEIR USE

[75] Inventor: Volker D. Arendt, Princeton, N.J.

[73] Assignee: American Cyanamid Company, Stamford, Conn.

[21] Appl. No.: 23,427

[22] Filed: Mar. 9, 1987

[51] Int. Cl.$^4$ ............... A61K 37/02; A61K 37/24; A61K 37/36

[52] U.S. Cl. ................................. 514/2; 514/12; 514/21; 514/806; 530/324; 530/399; 530/813; 530/814

[58] Field of Search ............... 514/2, 21, 806, 12; 530/324, 399, 813, 814

[56] References Cited

U.S. PATENT DOCUMENTS

| | | | |
|---|---|---|---|
| 3,947,352 | 3/1976 | Cuatrecasas et al. | 530/362 |
| 4,003,792 | 1/1977 | Mill et al. | 536/3 |
| 4,357,423 | 11/1982 | Cox et al. | 935/56 |
| 4,521,409 | 6/1985 | Bauman | 514/2 |
| 4,585,754 | 4/1986 | Meisner et al. | 435/178 |

Primary Examiner—John Kight
Assistant Examiner—Nathan M. Nutter
Attorney, Agent, or Firm—Alice C. Brennan

[57] ABSTRACT

The invention relates to compositions comprising adducts of activated polysaccharides with biologically active growth hormones, somatomedins, growth factors and biologically active fragments. The invention also relates to a method for increasing and maintaining increased levels of these biologically active molecules in the blood of treated animals for extended periods of time, increasing weight gains in animals, and increasing milk production of lactating animals by the administration of a composition of the invention.

21 Claims, No Drawings

SUSTAINED RELEASE COMPOSITIONS FOR PARENTERAL ADMINISTRATION AND THEIR USE

BACKGROUND OF THE INVENTION

The development of effective sustained release compositions containing complex biologically active molecules such as growth hormones requires the identification of systems which are biocompatible and do not interfere or interact with the activity of these molecules.

Recent developments in the area of administration of growth hormones include those described by S. L. Davis, et al., in The Journal of Dairy Science, Vol. 66, No. 9, pp 1980-1981 (1983) which describes the use of beeswax implants for the administration of the growth hormone oGH. A cholesterol matrix delivery system for the sustained release of macromolecules, including a variety of growth hormones, is described in U.S. Pat. No. 4,452,775. Injectable sustained release compositions include biodegradable polymer microcapsules containing aqueous solutions of polypeptides which are described in European Patent Application 81305426.9; a crystalline carbohydrate nanosphere matrix described by U. Schroder, *J. Immunological Methods*, 70, pp 127-132 (1984); prolonged release nonaqeuous compositions of polypeptides which are preferably associated with metals or metal compounds which may additionally contain antihydration agents dispersed in biocompatible oils, which are described in European Patent Application 85870135.2, published Apr. 4, 1986. Pending Application for United States Letters Patent of S. Cady, R. Fishbein, U. Schroder, H. Erickson and B. Probasco, Ser. No. 830,158, filed Mar. 20, 1986, and pending Application for United States Letters Patent of W. Steber, R. Fishbein and S. Cady, Ser. No. 895,608, filed Aug. 11, 1986, describe sustained release compositions of biologically active molecules utilizing water dispersible carbohydrate polymer-aqueous systems and solid fat and/or wax-oil systems respectively. Systained release compositions of proteins and enzymes coupled to polyethylene and polypropylene glycols are described in U.S. Pat. No. 4,179,337; and European Patent Application 85301032.0, which describes a coupled enzyme, urokinase. A review of soluble polymer-enzyme adducts by A. Abuchowski and F. Davis is presented in Chapter 13 of Enzymes as Drugs, John Wiley and Sons (1981). Analytical and separation methods for use in biochemistry have been developed utilizing affinity chromatography which takes advantage of specific naturally occurring biological affinities such as antigen-antibody attraction, which are imparted to the chromatography adsorbant by covalently bonding the binding component to an activated matrix on a fixed support such as glass beads. The availability of affinity chromatography media which may be activated to covalently bond biologically active macromolecules has resulted in research such as that reported by N. Sinha and A. Light in *The Journal of Biological Chemistry, Vol.* 250, No. 22, pp 8624-8629, (1975), which describes the refolding of reduced trypsinogen and trypsin immobilized on agarose beads upon reoxidation.

It is an object of this invention to provide sustained release compositions comprising adducts of growth hormones, somatomedins, growth factors and biologically active fragments thereof, convalently bonded to biologically compatable activated polysaccharides which are suitable for parenteral administration.

It is another object of this invention to provide a method for increasing and maintaining increased levels of growth hormones in the blood of treated animals and humans for extended periods of time and obtaining beneficial effects such as increasing weight gains, increasing milk production in lactating animals, increasing growth rate, increasing feed efficiency, increasing muscle size, decreasing body fat and improving lean meat to fat ratio by parenteral administration of the compositions of the invention.

SUMMARY OF THE INVENTION

The present invention is directed to sustained release compositions comprising adducts of growth hormones, growth factors, somatomedins, and biologically active fragments thereof, covalently bonded to activated polysaccharides.

The invention also includes compositions for parenteral administration to animals comprising an activated polysaccharide biologically active growth hormone, somatomedin, growth factor, and biologically active fragments or derivatives thereof; and a pharmaceutically and pharmacologically acceptable liquid vehicle.

The invention includes a method for increasing milk production in animals, particularly dairy cows, comprising parenterally administering compositions of the invention to the cows. The invention also includes a method for elevating and maintaining elevated blood levels of growth hormones, growth factors, somatomedins, and biologically active fragments thereof in humans or animals comprising parenterally administering compositions of the invention.

DETAILED DESCRIPTION OF THE PREFERRED EMBODIMENTS

Polysaccharides which are suitable for use in the compositions of this invention include naturally occurring and synthetic biologically compatable polysaccharides and derivatives thereof containing hydroxyl groups which may be activated by coupling with reactive groups that are capable of bonding with the biologically active agent. Methods for activating polysaccharides for immobilizing enzymes via imido carbonates, carbonates, oxiranes, aziridines and activated double bonds and halogens are described in *Methods in Enzymology Vo. XLIV*, Academic Press 1976. Preferred activated polysaccharides for use in composition of this invention are imido carbonates and carbonates of naturally occurring and synthetic polysaccharides.

In general the preferred polysaccharides are water dispersible carbohydrate polymers which upon dispersion in either aqueous or organic systems result in increased viscosity of the system and are frequently used as thickening or gelling agents. Preferred activated polysaccharides for the preparation of sustained release adducts of this invention include agarose, agar, cellulose, hemicellulose including xylan, carboxymethylcellulose, dextran, dextrinstraches including amylose, glucans like lichenin, nigeran and glycogens, fructans including inulin, galactans, mannans, polyuronides including gums and mucilages, fucoidin, and derivatives thereof.

Biologically active agents suitable for administration in the compositions of the invention include growth hormones, somatomedins, growth factors, and other biologically active fragments and derivatives thereof.

Preferred agents include bovine, ovine, equine, procine, avian and human growth hormones, and encompass those which are of natural, synthetic, recombinant or biosynthetic origin.

The sustained release adducts of this invention are administered by injection as a dispersion in a pharmaceutically and pharmacologically acceptable liquid vehicle. Vehicles suitable for use in administering compositions of this invention include both aqueous based, water miscible systems and water immiscible liquid vehicles. Aqueous vehicles suitable for the administration of the sustained release compositions of the invention include aqueous buffered systems such as phosphate buffered saline (PBS) which contains $NaH_2PO_4 \cdot H_2O$ (0.025 mol), $Na_2HPO_4$ (0.025 mol), and NaCl (0.15 mol) which has been adjusted to pH 7.1; and carbonate buffer saline (CBS) which contains $Na_2CO_3$ (0.025 mol), $NaHCO_3$ (0.025 mol), and NaCl (0.15 mol) which has been adjusted to pH 9.4; and saline; alone and in combination with other pharmaceutically and pharmacologically acceptable water miscible solvents which are frequently employed in biological preparations for parenteral administrations including a variety of liquid alcohols, glycols, esters, and amides. As such, these solvents find utility in the compositions of this invention. Pharmaceutically and pharmacologically acceptable water immiscible liquids suitable for use include oils, liquid fats, water immiscible alcohols and glycols or mixtures thereof. Immiscible vehicles are chosen as to both disperse and coat the activated polysaccharide adduct and also to provide an acceptable viscosity of the injection mixture. Preferred water immiscible vehicles for the administration of the compositions of this invention include fatty acid glycerides and blends thereof which are liquid at ambient temperatures such as synthetic oils and vegetable oils such as olive, sesame seed, peanut, sunflower seed, soybean, cottonseed, corn, safflower, palm, rapeseed and coconut; animal oils such as fish oils, fish liver oils, sperm oils, or fractions derived therefrom; and mixtures thereof.

Stabilizers, preservatives, surfactants, salts, buffers or mixtures thereof may be included in the injectable compositions of the invention with amounts of up to about 15% on a weight basis being preferred. Preferred stabilizers include dehydroacetic acid and salts thereof, the sodium salt being most preferred; salicylanilide, sorbic acid, boric acid, benzoic acid and salts thereof; sodium nitrite and sodium nitrate.

Preferred surfactants for use in injectable compositions of the invention are non-ionic in nature such as polyoxyethylene sorbitan mono-oleate (20 mols ethoxylation), and block copolymers of ethylene oxide and propylene oxide; amounts of about 0.1% to 10.0% on a weight basis being preferred.

Uniquely, it has been found that increased weight gains are obtained by injecting animals with the compositions of the invention in a suitable vehicle. In order to obtain beneficial and/or therapeutic effects of biologically active agents such as in increases in weight gain, growth rate, milk production in lactating animals and muscle size and to improve feed efficiency, decrease body fat and improve lean meat to fat ratio, elevated blood levels of the active ingredients are generally observed in test animals. Maintaining elevated blood levels is an indication of the slow release of the active ingredient. Properties such as increased milk production, growth rate, improved efficiency and increased lean meat are generally observed when elevated blood levels of the active ingredient are maintained. The invention includes the use of the compositions herein to improve milk production, increase growth rate, improve feed efficiency, increase lean meat in animals, increase and maintain levels of hormones in the blood stream of animals.

A preferred embodiment of this invention is the activation of the polysaccharide by formation of an imido carbonate and reaction of the activated polysaccharide with a growth hormone at ambient temperature. This procedure is illustrated graphically in Flow Diagram I below which depicts the formation of an activated polysaccharide imido carbonate by reaction with cyanogen bromide and subsequent formation of a growth hormone adduct.

FLOW DIAGRAM I

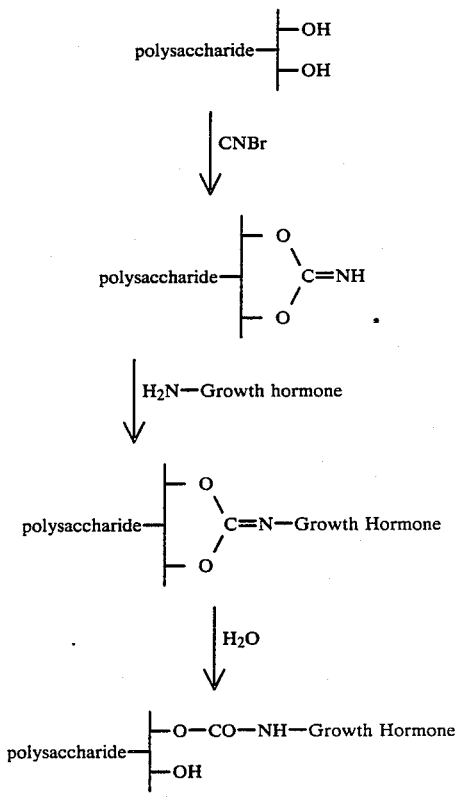

The resulting adduct may then be isolated by centrifugation, and washing and drying of the residue. The solid product is then ground to a particle size range about 20 to 70 microns and a portion assayed by nitrogen analysis to determine the percentage of growth hormone present. Utilizing the above procedure has yielded adducts with bovine growth hormone of about 60% to 80% on a weight basis.

*In vitro* dissolution experiments on an adduct of activated agarose and bovine growth hormone (68% loading) have shown that a total of 35% of the hormone is dissolved after 16 days.

Compositions of the invention have also demonstrated sustained growth through ten days in Hypophysectomized Rat Weight Gain Tests. The invention is further illustrated by the following non-limiting examples.

EXAMPLE 1

Preparation of bovine growth hormone-activated agarose adduct

Cyanogen bromide activated agarose powder (100 mg, source Sigma) is added to a stirred solution of recombinant bovine growth hormone (500 mg) in distilled water (20 mL) at room temperature. The resulting suspension is stirred for 16 hours. After this time the material is centrifuged, the supernatant liquid is decanted and the residue is washed twice with 20 mL distilled water. The solid product is dried at room temperature in a vacuum oven. The dry solid is broken up and passed through a 100 mesh sieve, to yield an adduct containing 75.4% bovine growth hormone.

Utilizing the above procedure yields the compositions listed in Table 1 below.

TABLE 1

Bovine Growth Hormone - Agarose Adduct

| Composition | 2 | 3 | 4 |
| --- | --- | --- | --- |
| Starting material bGH (mg) | 500 | 1,200 | 7,000 |
| Product | 1,000 | 2,400 | 14,000 |
| Yield (mg) | 449 | 1,371 | 7,000 |
| N Analysis (%) | 11.53 | 9.90 | 12.21 |
| bGH(%) | 74.4 | 64.0 | 78.7 |

EXAMPLE 2

Dissolution of bovine growth hormone-agarose adduct

A dissolution experiment is carried out in a constant temperature shaking bath containing vials with samples immersed in 30 mL of phosphate buffered saline. Solutions are replaced periodically and monitored for growth hormone by High Pressure Liquid Chromatography (HPLC). All solutions are run at 39° C. in buffered saline ($NaH_2PO_4 \cdot H_2O$ 3.45 g, $Na_2HPO_4$ 3.55 g, NaCl 9.5 g. diluted to 1000 mL) solution adjusted to pH 7.4.

The results of these experiment with a growth hormone-agarose adduct prepared by the procedure of Example 1, having 68% loading of hormone is summarized in Table II below.

TABLE 2

Dissolution of bovine growth hormone - agarose adduct

| Time Days | Cumulative % growth hormone release |
| --- | --- |
| 1 | 26.6 |
| 2 | 28.3 |
| 3 | 31.4 |
| 6 | 32.0 |
| 9 | 33.0 |
| 12 | 34.0 |
| 16 | 35.0 |
| 19 | 35.0 |
| 26 | 35.2 |

EXAMPLE 3

Effectiveness of injectable compositions of the invention

The efficacy of injectable compositions of this invention is demonstrated utilizing a hypophysectomized (hypox) rat assay. The hypophysectomized rat does not produce its own growth hormone and is sensitive to injected bovine growth hormone. The response measured is growth over a period of time such as ten days.

Each of the hypox albino rats (Taconic Farms, Sprague Dawley derived is injected with a sufficient quantity of composition 2 prepared in Example 1 to provide a ten-day dose of 800 micrograms (80 micrograms/day) of bovine growth hormone in 0.2 mL of PBS containing 2% carboxymethylcellulose.

Test Procedure

Prior to the test, the animals are wieghed and the animals to be used for the test are selected based on body weight. Only those animals whose body weights are one standard deviation from the mean body weight of the group are selected. The resulting group is then randomly divided into treatment groups consisting of eight rats/group by a computer generated randomization procedure. The test animals are then transferred to a clean cage and housed four rats/cage. On the initial day of the study the test animals are weighed and any animals with excessive weight gain or loss (±grams) are replaced. The animals are then assigned to test groups and treated.

At the end of the ten-day test period, total weight gain for each animal is recorded and the average weight gain per rat for each treatment determined. The results of these experiments, which are summarized in Table III below, demonstrate the effectiveness of injectable compositions of this invention.

TABLE III

Effectiveness of sustained release compositions of the invention for increasing weight gains

| Body weight (g) | | | | | | Weight gain (g) | | | | |
| --- | --- | --- | --- | --- | --- | --- | --- | --- | --- | --- |
| Day 0 | Day 2 | Day 4 | Day 7 | Day 10 | | Days 0-2 | Days 2-4 | Days 4-7 | Days 7-10 | Days 0-10 |
| 92 | 100 | 101 | 101 | 104 | | 8.0 | 1.0 | 0.0 | 3.0 | 12.0 |
| 96 | 103 | 106 | 105 | 111 | | 7.0 | 3.0 | −1.0 | 6.0 | 15.0 |
| 93 | 98 | 102 | 101 | 103 | | 5.0 | 4.0 | −1.0 | 2.0 | 10.0 |
| 94 | 100 | 100 | 105 | 103 | | 6.0 | 0.0 | 5.0 | −2.0 | 9.0 |
| 95 | 102 | 104 | 105 | 102 | | 7.0 | 2.0 | 1.0 | −3.0 | 7.0 |
| 87 | 92 | 96 | 100 | 101 | | 5.0 | 4.0 | 4.0 | 1.0 | 14.0 |
| 89 | 95 | 100 | 101 | 103 | | 6.0 | 5.0 | 1.0 | 2.0 | 14.0 |
| 92 | 99 | 101 | 104 | 106 | | 7.0 | 2.0 | 3.0 | 2.0 | 14.0 |
| Total (g) 92.3 | 98.6 | 101.3 | 102.8 | 104.1 | Average (g) | 6.4 | 2.6 | 1.5 | 1.4 | 11.9 |
| Standard deviation (g) 3.0 | 3.6 | 3.0 | 2.2 | 3.1 | Standard deviation (g) | 1.1 | 1.7 | 2.3 | 2.8 | 2.9 |

What is claimed is:

1. A biologically active sustained release composition consisting essentially of an adduct of a growth hormone, growth factor, somatomedin or biologically active fragment thereof, covalently bonded through a carbamate or carbonate linkage to an activated polysaccharide.

2. A composition according to claim 1 wherein the activated polysaccharide is an imido carbonate or carbonate of a natural or synthetic polysaccharide.

3. A composition according to claim 2 wherein the activated polysaccharide is covalently bonded to a growth hormone of bovine, ovine, equine, porcine, avian or human growth hormone of natural, synthetic, recombinant or biosynthetic origin.

4. A composition according to claim 3 wherein the activated polysaccharide is an imido carbonate of agarose, agar, cellulose, hemicellulose, carboxymethylcellulose, dextran, dextrin-starches, fructans, galactans, mannans, polyuronides, fucoidin or derivatives thereof.

5. A composition according to claim 4 wherein the activated polysaccharide is an imido carbonate of agarose and the growth hormone is bovine growth hormone.

6. A biologically active injectable sustained release composition consisting essentially of an adduct of a growth hormone, growth factor, somatomedin or biologically active fragment thereof; covalently bonded through a carbamate or carbonate linkage to an activated polysaccharide dispersed in a pharmaceutically and pharmacologically acceptable liquid vehicle.

7. A composition according to claim 6 wherein the vehicle is a water miscible liquid of saline, buffered saline or a water miscible alcohol, glycol, ester, amide or a water miscible mixture thereof, or a water immiscible oil, liquid fat, or a water immiscible alcohol, glycol, or water immiscible mixture thereof.

8. A composition according to claim 7 containing about 0% to 15% on a weight basis of stabilizers, preservatives, surfactants, salts, buffers or a mixture thereof.

9. A composition according to claim 8 wherein the activated polysaccharide is an imido carbonate or carbonate of a natural or synthetic polysaccharide.

10. A composition according to claim 9 wherein the activated polysaccharide is covalently bonded to a growth hormone of bovine, ovine, equine, porcine, avian or human growth hormone of natural, synthetic, recombinant or biosynthetic origin.

11. A composition according to claim 10 wherein the activated polysaccharide is an imido carbonate of agarose, agar, cellulose, hemicellulose, carboxymethylcellulose, dextran, dextrin-starches, fructans, galactans, mannans, polyuronides, fucoidin or derivatives thereof.

12. A composition according to claim 11 wherein the activated polysaccharide is an imido carbonate of agarose and the growth hormone is bovine growth hormone.

13. A method for elevating and maintaining elevated blood levels of a biologically active growth hormone, growth factor, somatomedin or a biologically active fragment thereof for the purpose of increasing weight gain, growth rate, milk production or muscle size, improving feed efficiency, or decreasing body fat and improving lean meat to fat ratio in an animal comprising parenterally administering to the animal an effective amount of a biologically active injectable sustained release composition consisting essentially of an adduct of a growth hormone, growth factor, somatomedin, or a biologically active fragment thereof, covalently bonded through a carbamate or carbonate linkage to an activated polysaccharide dispersed in a pharmaceutically and pharmacologically acceptable liquid vehicle.

14. A method according to claim 13 wherein the vehicle is a water miscible liquid of saline, buffered saline or a water miscible alcohol, glycol, ester, amide, or a water miscible mixture thereof, or a water immiscible oil, liquid fat, or a water immiscible alcohol, glycol, or water immiscible mixture thereof.

15. A method according to claim 14 wherein the composition contains about 0% to 15% on a weight basis of stabilizers, preservatives, surfactants, salts, buffers or a mixture thereof.

16. A method according to claim 15 wherein the activated polysaccharide is covalently bonded to a growth hormone of bovine, ovine, equine, porcine, avian or human growth hormone of natural, synthetic, recombinant or biosynthetic origin.

17. A method according to claim 16 wherein the activated polysaccharide is an imido carbonate of agarose, agar, cellulose, hemicellulose, carboxymethylcellulose, dextran, dextrin-starches, fructans, galactans, mannans, polyuronides, fucoidin, or derivatives thereof.

18. A method according to claim 17 wherein the activated polysaccharide is an imido carbonate of agarose and the growth hormone is bovine growth hormone.

19. A composition according to claim 4 wherein said hemicellulose comprises xylan; said dextrin-starches comprise amylose, glucans like lichenin, nigeran or glycogens; said fructans comprise inulin; and said polyuronides comprise gums or mucilages.

20. A composition according to claim 11 wherein said hemicellulose comprises xylan; said dextrin-starches comprise amylose, glucans like lichenin, nigeran or glycogens; said fructans comprise inulin; and said polyuronides comprise gums or mucilages.

21. A method according to claim 17 wherein said hemicellulose comprises xylan; said dextrin-starches comprise amylose, glucans like lichenin, nigeran or glycogens; said fructans comprise inulin; and said polyuronides comprise gums or mucilages.

* * * * *